(12) United States Patent
Zastrow

(10) Patent No.: US 11,007,034 B2
(45) Date of Patent: May 18, 2021

(54) DEVICE FOR GUIDING A DENTAL SURGICAL HOLLOW MILLING MACHINE AND A METHOD FOR PRODUCING SUCH A DEVICE

(71) Applicant: Frank Zastrow, Heidelberg (DE)

(72) Inventor: Frank Zastrow, Heidelberg (DE)

(*) Notice: Subject to any disclaimer, the term of this patent is extended or adjusted under 35 U.S.C. 154(b) by 65 days.

(21) Appl. No.: 15/902,553

(22) Filed: Feb. 22, 2018

(65) Prior Publication Data

US 2018/0235726 A1 Aug. 23, 2018

(30) Foreign Application Priority Data

Feb. 22, 2017 (DE) ...................... 10 2017 202 817.3

(51) Int. Cl.
| | |
|---|---|
| *B33Y 50/00* | (2015.01) |
| *A61C 1/08* | (2006.01) |
| *A61B 17/17* | (2006.01) |
| *A61C 8/00* | (2006.01) |
| *A61C 8/02* | (2006.01) |
| *A61B 17/16* | (2006.01) |

(52) U.S. Cl.
CPC ............ *A61C 1/082* (2013.01); *A61B 17/176* (2013.01); *A61C 8/0089* (2013.01); *A61B 17/1635* (2013.01); *A61C 8/0006* (2013.01); *B33Y 50/00* (2014.12)

(58) Field of Classification Search
CPC ..... A61C 1/082; A61C 8/0089; A61C 8/0006; A61C 1/16; A61B 17/176; A61B 17/1635; B33Y 50/00
See application file for complete search history.

(56) References Cited

U.S. PATENT DOCUMENTS

| | | | |
|---|---|---|---|
| 2010/0081107 A1* | 4/2010 | Bagambisa | A61C 8/0089 433/75 |
| 2010/0185201 A1* | 7/2010 | Kim | A61C 1/084 606/80 |
| 2016/0106513 A1 | 4/2016 | De Stavola et al. | |
| 2016/0157960 A1 | 6/2016 | Lin | |

FOREIGN PATENT DOCUMENTS

| | | |
|---|---|---|
| DE | 10 2010 048 090 A1 | 4/2012 |
| DE | 10 2012 102 255 A1 | 9/2012 |
| FR | 2 882 250 A1 | 8/2006 |
| WO | 2014/188369 A1 | 11/2014 |
| WO | 2016/188522 A1 | 12/2016 |

* cited by examiner

*Primary Examiner* — Heidi M Eide
*Assistant Examiner* — Drew S Folgmann
(74) *Attorney, Agent, or Firm* — Seed Intellectual Property Law Group LLP

(57) ABSTRACT

A device for guiding a dental-surgical hollow bur during a bone extraction, having a template that can be fixed in the region of a extraction point and having at least one guiding means arranged on the template, wherein the guiding means guides the hollow bur such that only a portion of the distal edge of the hollow bur can be brought into contact with the bone. Furthermore, a method for producing such a device is specified.

20 Claims, 20 Drawing Sheets

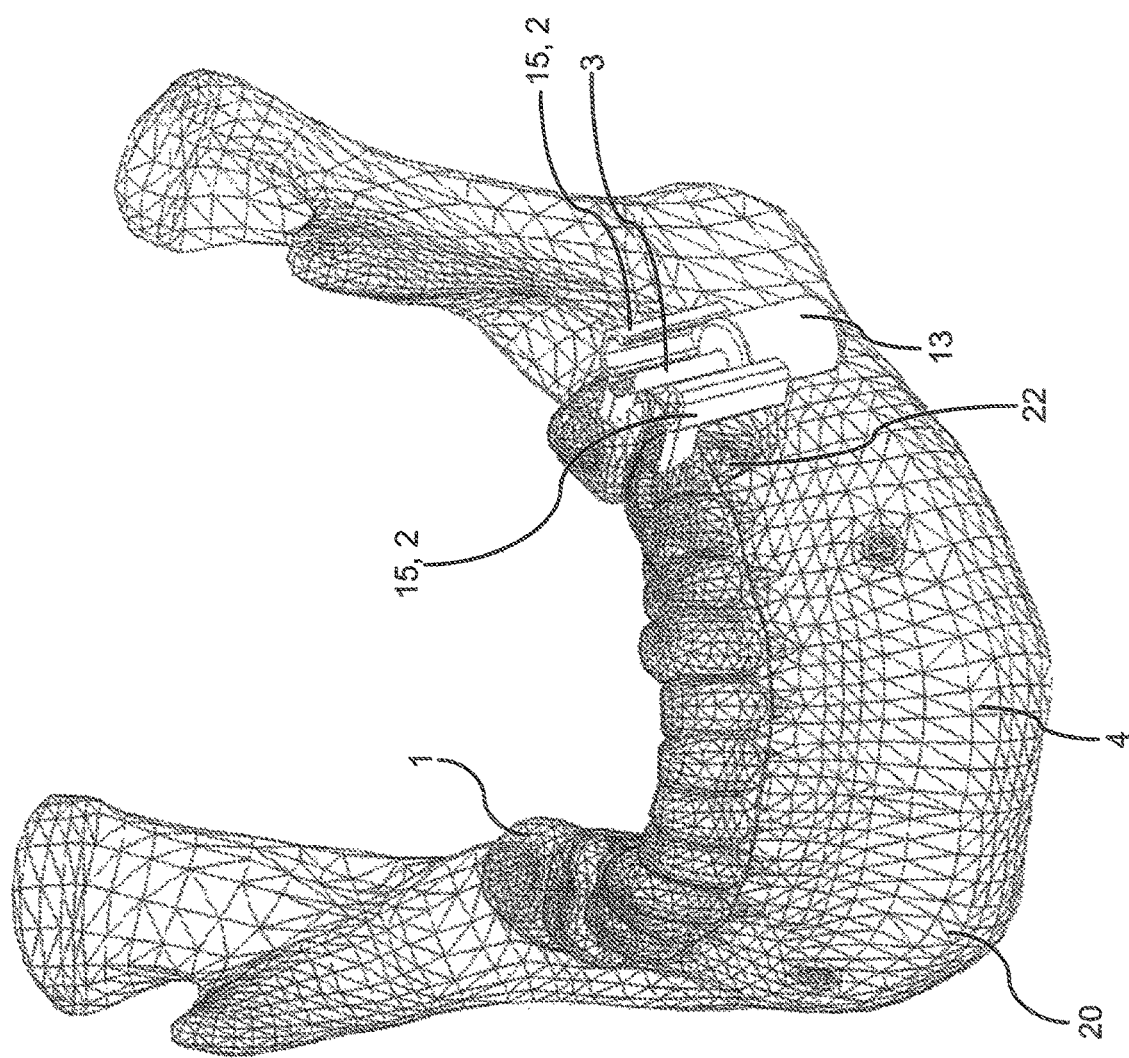

DEVICE FOR GUIDING A DENTAL SURGICAL HOLLOW MILLING MACHINE AND A METHOD FOR PRODUCING SUCH A DEVICE

BACKGROUND

Technical Field

The present disclosure relates to a device for guiding a dental-surgical hollow bur during a bone extraction. The present disclosure furthermore relates to a guiding means and a template for such a device. The disclosure moreover relates to a method for producing such a device.

Description of the Related Art

Dentists performing surgeries, oral surgeons, and maxillofacial surgeons are often faced with the challenge that bone has been lost in the oral cavity as a result of bone atrophy, accidents, periodontitis, or tooth extraction.

When dental implants are planned in order to insert new teeth, it is important that these bone deficits be constructed before or at the same time the implant is placed, so that the dental implants once again have a new foundation and a stable support.

Autologous, patient's own bone is still considered to be the gold standard in bone grafting procedures. This is due to the properties of the bone, since autologous bone combines osteogenic, osteoinductive, and osteoconductive properties. This means that the bone has the potency to generate its own bone tissue and form its own vessels, and, moreover, acts as a guide structure for newly generated bone. In contrast to autologous bone, bone replacement material does not have any biological potency and therefore acts only osteoconductively, i.e., it also acts as a guiding rail.

Various methods for working with autologous bone are already known. In the case of larger bone deficits, toothless bone areas basically lend themselves as secondary intraoral extraction points—alternative to the maxillary tuber, the anterior nasal spine, the palate, the region of the maxillary sinus wall in the upper jaw, or else the lower jaw—since they are of a rather cortical nature, and the bone quality is considered to be very good and stable. There are various bone extraction points in the lower jaw, e.g., again toothless areas, the chin, or the retromolar region.

The bone extraction may in this case take place using various instruments. The concept of the bone extraction is thereby mostly similar.

Three to four predetermined breaking points are created using either a so-called Lindemann bur or a piezosurgery device, or, alternatively, a small saw, and the block is subsequently broken out using a chisel or another instrument. This is disadvantageous in that more or less great force needs to be applied to the jaw during bone extraction. This procedure is therefore somewhat dreaded by the physician, for the reason, as well, that this hammering or breaking of the bone block out of the respective region is also uncomfortable for the patient.

Dentists are accustomed to rotary instruments and drills because of their profession. Use of the so-called trephine bur or hollow bur, which is put on a handpiece and has a head that is designed as a hollow cylinder, has also become established in this way. Teeth for machining the bone are formed on the distal edge of the head. Trephine burs or hollow burs are, for example, used for implant bed processing and have a diameter of approximately 3 mm to 4 mm. Using these burs, extremely small and narrow drilling cylinders are removed, which are only conditionally suitable for bone construction.

In the case of the aforementioned devices, approximately three to four cuts or predetermined breaking points must be created for the bone extraction in order to obtain the necessary piece of bone. This causes great stress for the patient and requires great technical skill on the part of the operator. In the process, it must, in particular, be kept in mind that the surrounding soft tissue, e.g., the cheek or lip, is not injured by the surgical tool.

BRIEF SUMMARY AND INITIAL DESCRIPTION

The present disclosure is based upon the aim of specifying a device such that a reliable and gentle tooth extraction is possible for the patient, by structurally simple means. Furthermore, a method for producing such a device is to be specified.

According to the present disclosure, the above aim is achieved by the features of claim 1. Accordingly, a device for guiding a dental-surgical hollow bur during a bone extraction is specified, having a template that can be fixed in the region of an extraction point and having at least one guiding means arranged on the template, wherein the guiding means guides the hollow bur such that only a portion of the distal edge of the hollow bur can be brought into contact with the bone.

In a manner according to the present disclosure, it was first realized that the underlying aim can be achieved by a template having a guiding means for guiding a dental-surgical hollow bur in a sophisticated manner. In doing so, the template can be fixed in the region of the extraction point. On the template is arranged a guiding means that guides the hollow bur at an exactly defined angle to the extraction point, so that only a portion of the distal edge of the rotary hollow bur can be brought into contact with the bone for bone extraction. In concrete terms, the hollow bur can, in the process, be guided laterally along the bone, so that a piece of bone in the shape of a circular segment is extracted. This ensures that the hollow bur can be introduced into the extraction point in a guided movement by the operator—in particular, at an exact angle.

In another manner according to the present disclosure, it has been recognized that, contrary to a preconception in professional circles, a hollow bur is suitable not just for removing small drilling cylinders. Rather, an appropriately designed hollow bur can be used to "cut away" the required piece of bone or bone segment from the bone. As a result of the guiding means arranged on the template, the hollow bur can be brought into contact with the bone of the extraction point in just such a way. In other words, only a circular arc of the distal edge of the head of the hollow bur can be brought into contact with the bone and thus serves as an effective operating area. In contrast to the instruments and tools known from the prior art, there is no need to make three to four cuts or predetermined breaking points. Rather, only a single predetermined breaking point results; a hammering-out of the bone is not necessary. The block produced can then be extracted or luxated without applying greater force, which is more gentle and comfortable for the patent compared to the known devices and techniques. The stress for the patient from the procedure is, consequently, minimal.

At this point, it is pointed out that the "distal edge" of the hollow bur is the region of the hollow cylindrical head of the hollow bur with which the bone is machined, i.e., cut, ground, or severed. The term, "hollow bur," is to be understood in the broadest sense; it can, for example, have saw teeth and/or diamond cuts in the operating area and can be coupled to a dental handpiece in order to be caused to rotate. The "extraction point" is the region of the bone from which the required piece of bone is separated. The "bone deficit" is the region of the bone that is to be reconstructed by the extracted bone segment.

In concrete terms, the template can be designed to be fixable in the upper jaw and/or in the lower jaw in a form-fit and/or force-fit manner. It is conceivable in this respect that the template be at least partially designed as a rail and/or can be fixed via holding pins or screws. The template can generally be realized in a bone- and/or tooth- and/or mucous membrane-supported manner. It is also conceivable that the template be fixed via an external fixing device that, for example, lies against the head of the patient.

In order to extract bone from several extraction points, several guiding means can be formed on the template. In this way, the hollow bur can be brought into contact with the bone at different extraction points through the guiding means. With structurally simple means, it is thus possible to extract a larger amount of bone.

The guiding means can, in an advantageous manner, surround the hollow bur such that the tissue surrounding the extraction point does not come into contact with the hollow bur. The guiding means thus serves, not only to bring the hollow bur into contact with the bone in a defined position, but also as a protective element, which shields the surrounding tissue from the hollow bur.

It is furthermore conceivable that the guiding means can be designed as a guiding sheath into which the hollow bur can be introduced. The guiding sheath can have a lateral opening so that a portion of the distal edge of the hollow bur can be brought into contact with the bone through the opening of the guiding sheath. By designing the guiding means as a guiding sheath, the surrounding soft tissue is optimally protected against injuries caused by the hollow bur. At this point, it is pointed out that the term, "guiding sheath," is to be understood in the broadest sense. The guiding sheath need, for example, not necessarily be designed to be round or as part of a circular cylinder, but can also, at least in sections, have an angular geometry. In a particularly advantageous manner, the guiding sheath can be closed at its end region, thus having a bottom. This, again, ensures that the surrounding tissue is protected. In a design of the guiding means as guiding sheath, it is advantageous for the hollow bur to have a spacer element that corresponds to the inner diameter of the guiding sheath and is rotatably coupled to the hollow bur. The hollow bur is thus rotatable in the guiding sheath, and having the distal end of the hollow bur come into contact with the guiding sheath is avoided.

Alternatively or additionally, the guiding means can have an—in particular, substantially cylindrical—receptacle for a corresponding guiding element of the hollow bur. The guiding element of the hollow bur can, for example, be a guiding pin extending in the axial direction from the bottom to the head of the hollow bur. The receptacle can be designed as a sheath or tube corresponding to the guiding pin. It is also conceivable that the guiding means of the template can be engaged in a corresponding guiding element of the hollow bur. For example, a guiding element—in particular, a rail—that is rotatably coupled to the hollow bur and corresponds to the guiding means, e.g., a rail, can be provided.

In order to ensure that the hollow bur does not penetrate too deeply into the bone, a depth stopper, in the sense of a depth stop for the hollow bur, can be formed on the guiding means.

The guiding means—in particular, the guiding sheath—can, advantageously, be detachably connected to the template. For example, coupling elements that correspond with each other and via which the guiding means can be fixed on the template at the desired angle can be provided on the guiding means—in particular, the guiding sheath—and on the template. The corresponding coupling elements can, for example, be designed as female and male parts. It is furthermore advantageous to produce the guiding means—in particular, the guiding sheath—from metal, so that it can be reprocessed for repeated use. Coupling elements can furthermore advantageously be provided at different regions of the template, so that the guiding means can be fixed on the template at the respectively required angle at different regions of the base element, and bone can thus be extracted at different extraction points.

It is furthermore conceivable that the guiding means—in particular, the guiding sheath—be designed as a single piece with the template or as an integral part of the template—for example, be glued, welded, etc.—to it. In a one-piece design, several guiding means—in particular, guiding sheaths—can be provided at different regions of the base element.

According to another embodiment, the template can have a holding means, in order to hold the extracted piece of bone in the region of a bone deficit to be constructed. The piece of bone may, specifically, be connectable to the template in a form-fit and/or force-fit manner—for example, be clipped to or clamped in it. This enables the operator to fix the piece of bone in the desired position in the region of the bone deficit—in particular, to screw it to the jaw bone to be constructed.

In a particularly advantageous manner, the guiding means—in particular, the guiding sheath—can be arranged or designed such that a hollow bur, the head of which has an outer diameter of 5 mm to 11 mm—preferably, 6 mm to 8 mm—and/or a depth of 6 mm to 17 mm—in particular, 9 mm to 14 mm—can be used with the template according to the present disclosure. In another advantageous manner, the guiding means—in particular, the guiding sheath—can be arranged or designed such that the circular arc of the distal edge of the hollow bur, which can be brought into contact with the bone, forms a circular segment that has a segment height of 2.0 mm to 3.5 mm—preferably, 2.2 mm to 2.5 mm.

The underlying aim is furthermore achieved by a guiding means according to claim 10. Accordingly, a guiding means for a device according to one of claims 1 through 9 is specified, having a coupling element for preferably detachably fixing it on a template. The coupling element may also be a defined region of the guiding means, which is glued or screwed to the template or can otherwise be fixed on it. The coupling element may, moreover, be a female or male part that can be engaged in a corresponding male or female part of the template.

The underlying aim is furthermore achieved by a template according to claim 11. Accordingly, a template for a device according to one of claims 1 through 9 is specified, having a coupling element for preferably detachably fixing a guiding element. The coupling element may also be a defined region of the template, which is glued or screwed to the guiding means or can otherwise be fixed on it. The coupling element may, moreover, be a female or male part that can be engaged in a corresponding male or female part of the guiding means.

The guiding means and/or the template may be designed according to the guiding means described in claims 1 through 9 or the template described there and may have the features and advantages previously mentioned with respect to this guiding means and/or this template. The guiding means according to claim 10 and the template according to claim 11 may, moreover, have individual or all features of the guiding means described in the following figure description or in the described template.

The underlying aim is, moreover, achieved by the method having the features of claim 12. Accordingly, a method for producing a device according to one of claims 1 through 9 having the following method steps is specified:

carrying out a three-dimensional, imaging process of the extraction point and, where appropriate, of the bone deficit—in particular, of the upper and/or lower jaw— in order to obtain three-dimensional data, creating a three-dimensional computer model of the extraction point and, where appropriate, of the bone deficit, using the three-dimensional data, and producing a template based upon the three-dimensional computer model.

In the manner according to the present disclosure, a three-dimensional imaging process is first carried out at the extraction point and, where appropriate, at the bone deficit. The extraction point may, in particular, be the upper and/or lower jaw. Using the three-dimensional data obtained by this process, a three-dimensional computer model of the extraction point and, where appropriate, of the bone deficit is created in a further manner according to the present disclosure. This is advantageous in that the bone extraction can be planned virtually—in particular, taking into account the individual anatomy of the patient, e.g., the course of the nerves, root canals, etc. Based upon this three-dimensional computer model, the patient-specific template is, in a further manner according to the present disclosure, then planned or produced. Based upon the three-dimensional computer model, the extraction point, and thus the positioning of the guiding means, can, furthermore, be determined precisely. For example, the template can be produced by means of a rapid prototyping process—in particular, a stereolithography process or a 3-D printing process. Any processes suitable for this purpose and known, in particular, in dental technology may be used. If the guiding means is designed to be a single piece with the template, it can be produced together with the template in the same work step, viz., based upon the three-dimensional computer model. If the guiding means is not an integral part of the template, the coupling elements can be produced on the template on the basis of the three-dimensional computer model, so that the guiding means can be fixed in the desired, defined position on the template, using the corresponding coupling elements.

Computer tomography and/or magnetic resonance tomography and/or digital volume tomography can, advantageously, be used as the three-dimensional imaging process.

The present disclosure furthermore relates to a dental-surgical hollow bur, wherein a spacer element is rotatably coupled to the hollow bur. This achieves that the hollow bur cannot be brought into contact with the guiding means according to the present disclosure. The hollow bur according to the present disclosure can, advantageously, have the features disclosed in the following figure description and the corresponding figures or individual features thereof.

BRIEF DESCRIPTION OF THE SEVERAL VIEWS OF THE DRAWINGS

There are various options for advantageously designing and developing the teaching of the present disclosure. To this end, reference is made, on the one hand, to the claims subordinate to claim 1 and, on the other, to the following description of preferred exemplary embodiments of the present disclosure based upon the drawing, based upon which the method according to the present disclosure is also described. Generally preferred designs and developments of the teaching are also explained in conjunction with the explanation of the preferred exemplary embodiments of the present disclosure with reference to the drawing. In the drawings:

FIG. 20 shows another schematic, perspectival view of the exemplary embodiment according to FIG. 18.

DETAILED DESCRIPTION

Figure 1:
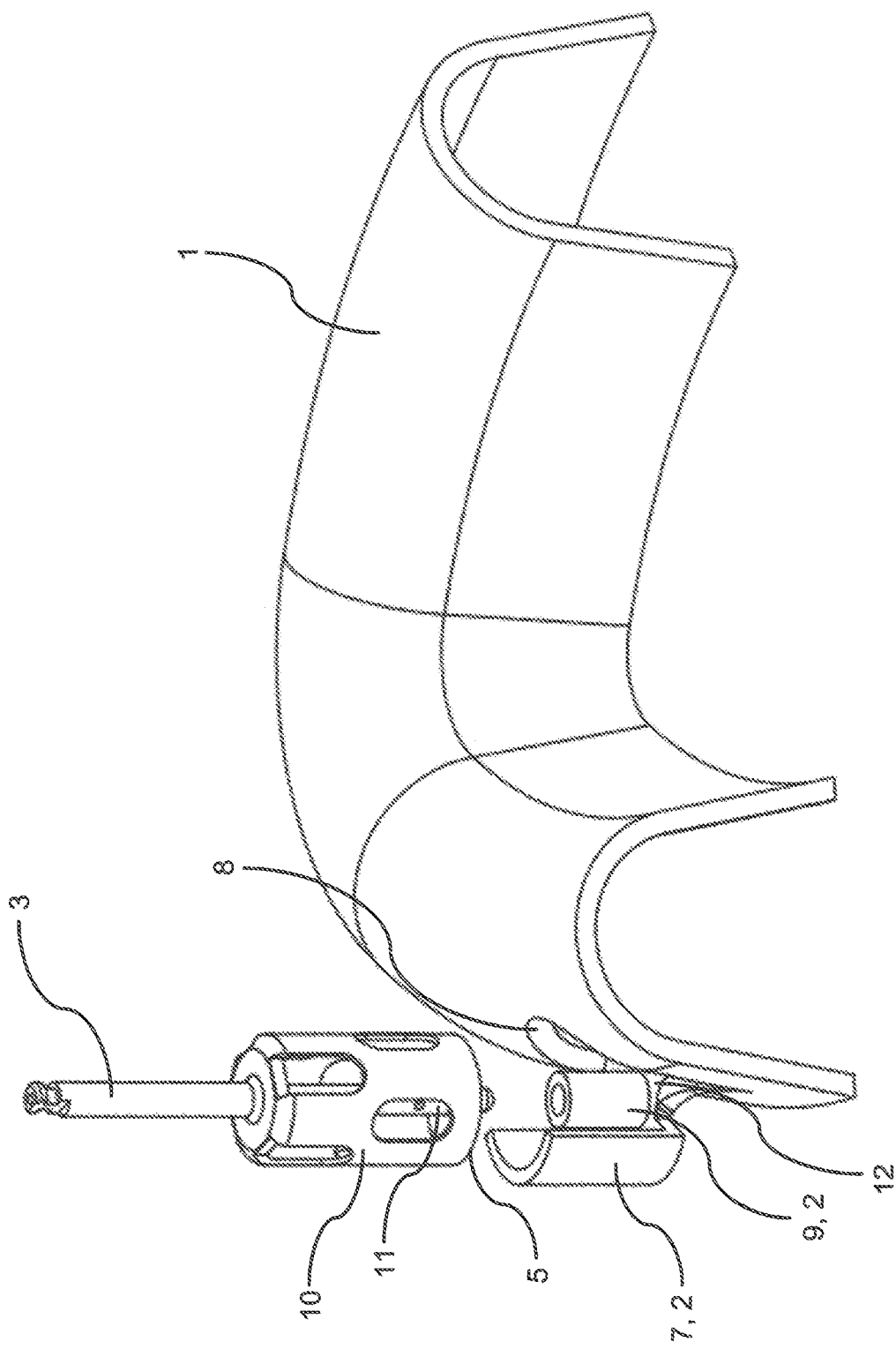
FIG. 1 shows a schematic, perspectival view of a first exemplary embodiment of a device according to the present disclosure.
Figure 2:
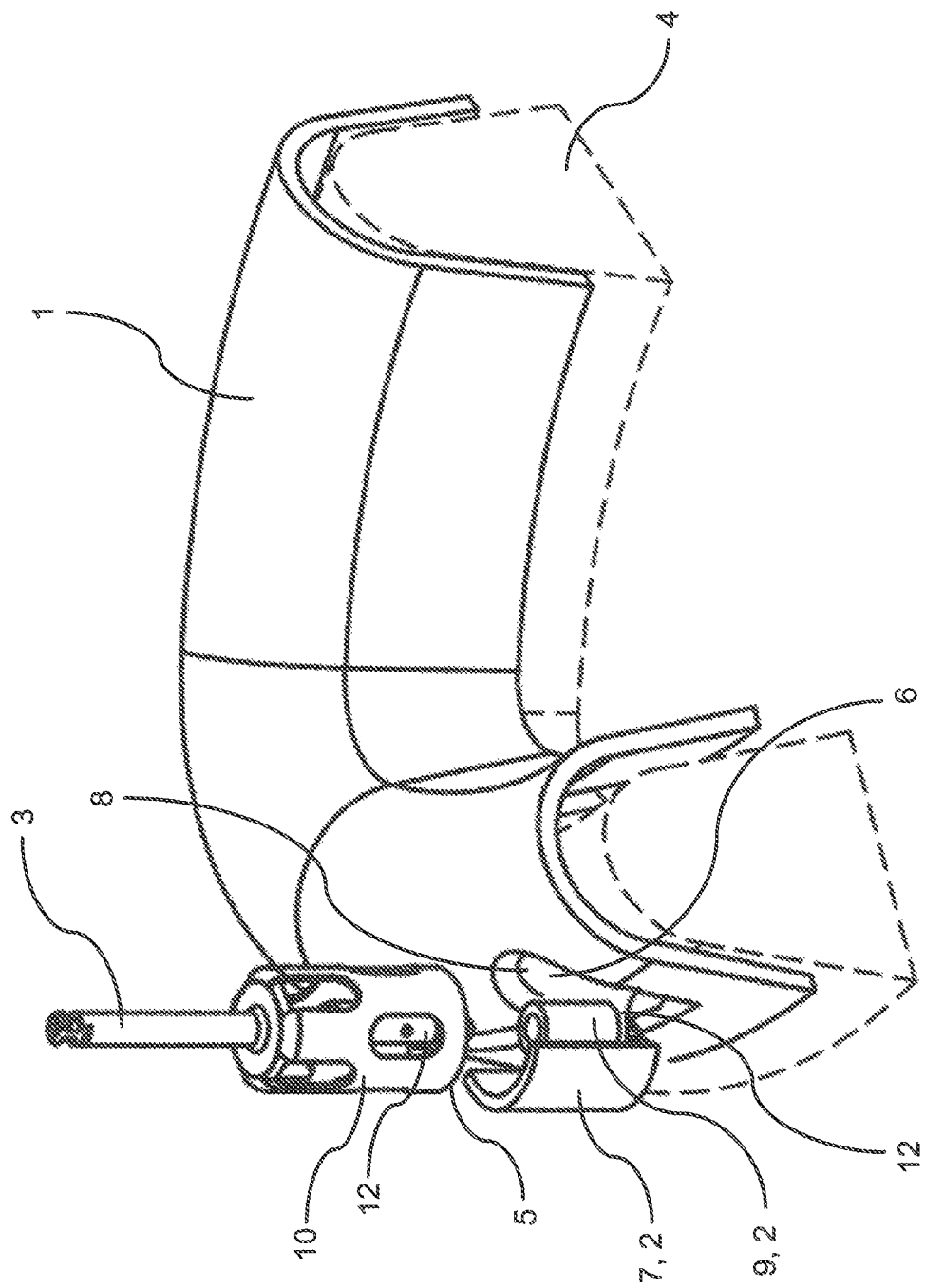
FIG. 2 shows another schematic, perspectival view of the exemplary embodiment according to FIG. 1.

FIGS. 1 and 2 show a first exemplary embodiment of a device according to the present disclosure. The device has a template 1, on which a guiding means 2 for a hollow bur 3 is formed. FIG. 2 schematically shows a jaw bone 4, on top of or on which the template 1 is arranged. It is pointed out that the template 1 does not necessarily have to abut the jaw bone 4, but can alternatively or additionally abut the existing teeth, the gums, etc. In this case, it can be clearly seen that the guiding means 2 is provided on the template 1 such that only a portion of the distal edge 5 of the hollow bur 3 can, in a defined position, be brought into contact with the bone 4 at the extraction point 6. Specifically, the guiding means 2 is designed such that the hollow bur 3 is guided laterally along the jaw bone 4.

The guiding means 2 is designed as guiding sheath 7, wherein the guiding sheath 7 is not completely closed. In addition to guiding the hollow bur 3, the guiding sheath 7 additionally serves to protect the surrounding tissue and can also be designed to be closed, wherein an opening 8 must be provided, through which the hollow bur 3 can be brought into contact with the bone 4. The inner diameter of the guiding sheath 7 is preferably, moreover, to be dimensioned such that the rotary hollow bur 3 does not come into contact with the guiding sheath 7.

The guiding means 2, moreover, comprises a cylindrical receptacle 9, which is realized as a circular cylinder or tube and serves to introduce a guiding element 11, or guiding pin, extending within the head 10 of the hollow bur 3. The receptacle 9 thus acts as a compulsory guide for the hollow bur 3. At this point, it is pointed out that the guiding means 2 does not necessarily have to have the guiding sheath 7, but can be realized by the receptacle 9 alone.

The guiding means 2 may also be designed detachably with the template 1. Moreover, a depth stopper 12 is formed, which serves as a depth stop so that the hollow bur 3 can be introduced into the jaw bone 4 only over a defined length.

Figure 3:
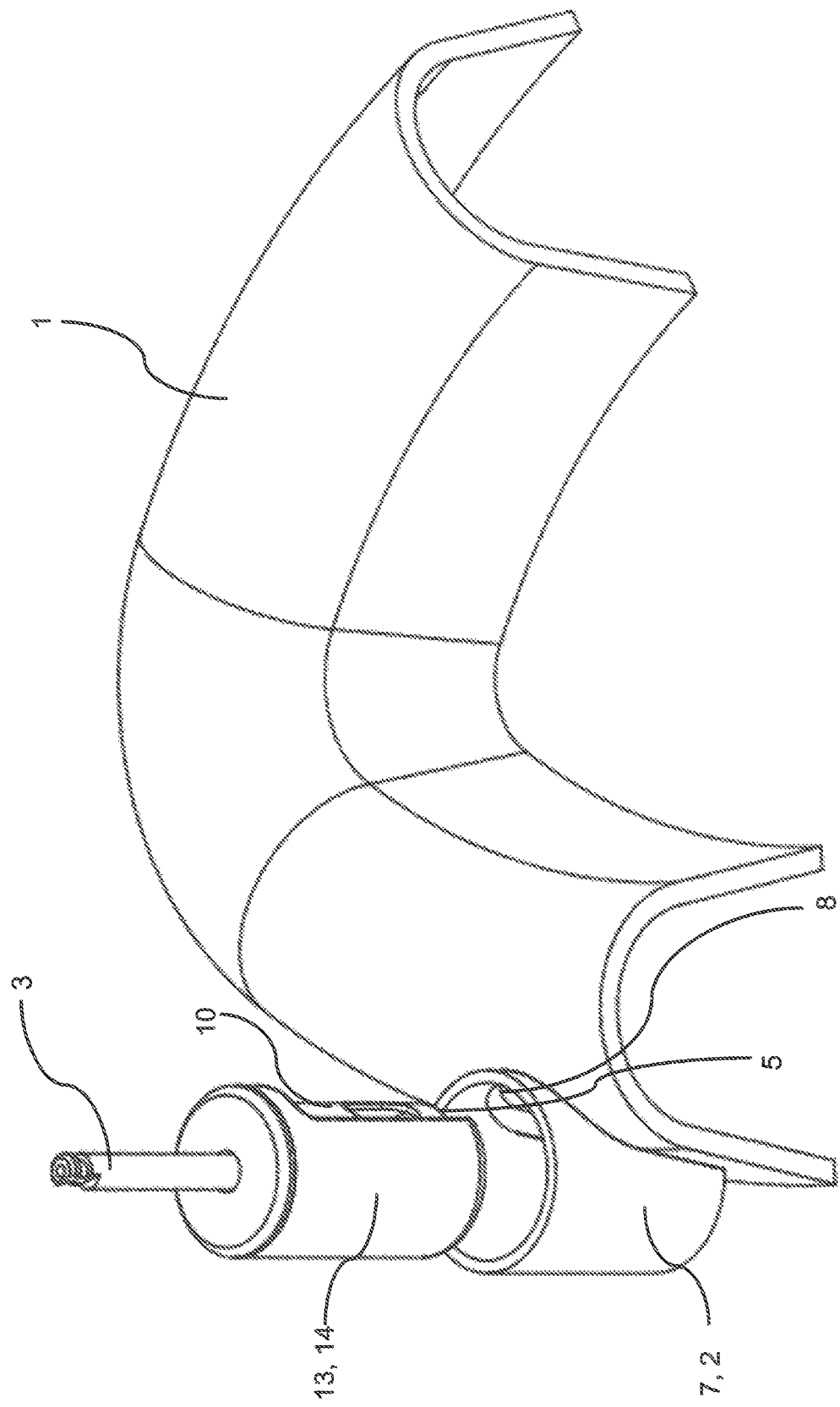
FIG. 3 shows a schematic, perspectival view of another exemplary embodiment of a device according to the present disclosure.
Figure 4:
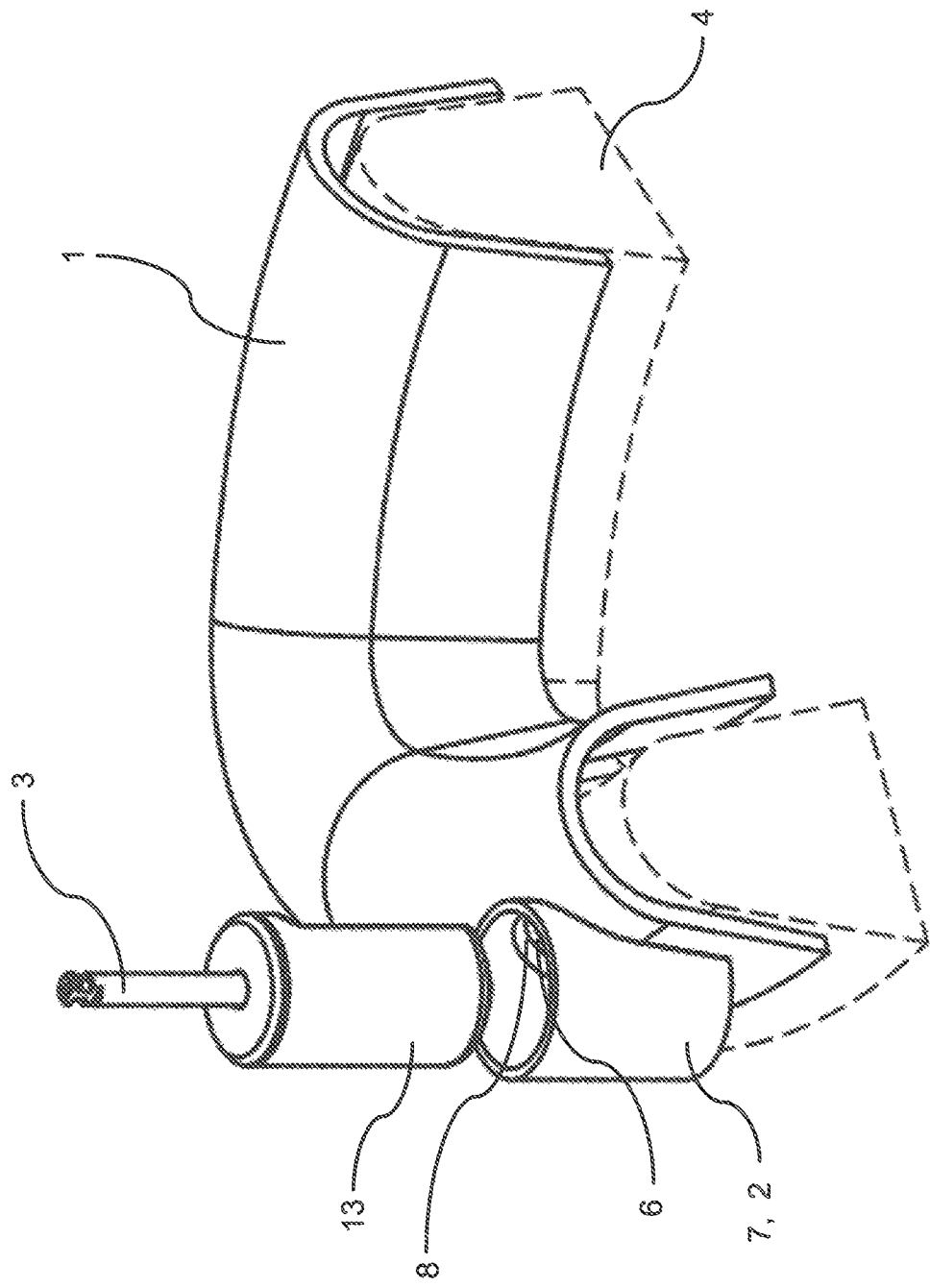
FIG. 4 shows another schematic, perspectival view of the exemplary embodiment according to FIG. 3.

FIGS. 3 and 4 show another exemplary embodiment of a device according to the present disclosure. In this case, the guiding means 2 is designed as guiding sheath 7 closed in the direction of the surrounding tissue, wherein the guiding sheath 7 is open laterally in the direction of the extraction point 6. A portion of the distal edge 5 can thus process the bone 4. In the exemplary embodiment shown here, the guiding sheath 7 is designed as a single piece with the base element 1. The guiding sheath 7 may, however, have coupling elements, via which it can be connected detachably to the base element 1.

The hollow bur 3 is rotatably coupled to a protective device 13 and can be introduced into the guiding sheath 7 together with the protective device 13. The protective device 13 has a lateral opening and serves as spacer element 14, so that the head 10 does not come into contact with the guiding sheath 7 or the template 1. Contrary to the illustration, the guiding sheath 7 does not necessarily have to be designed to be closed. It is sufficient if the guiding sheath 7 surrounds the protective device 13 only partially. Furthermore, the exemplary embodiment according to FIGS. 3 and 4 corresponds to the exemplary embodiment shown in FIGS. 1 and 2, so that reference is made to the explanations above in order to avoid repetition.

Figure 5:
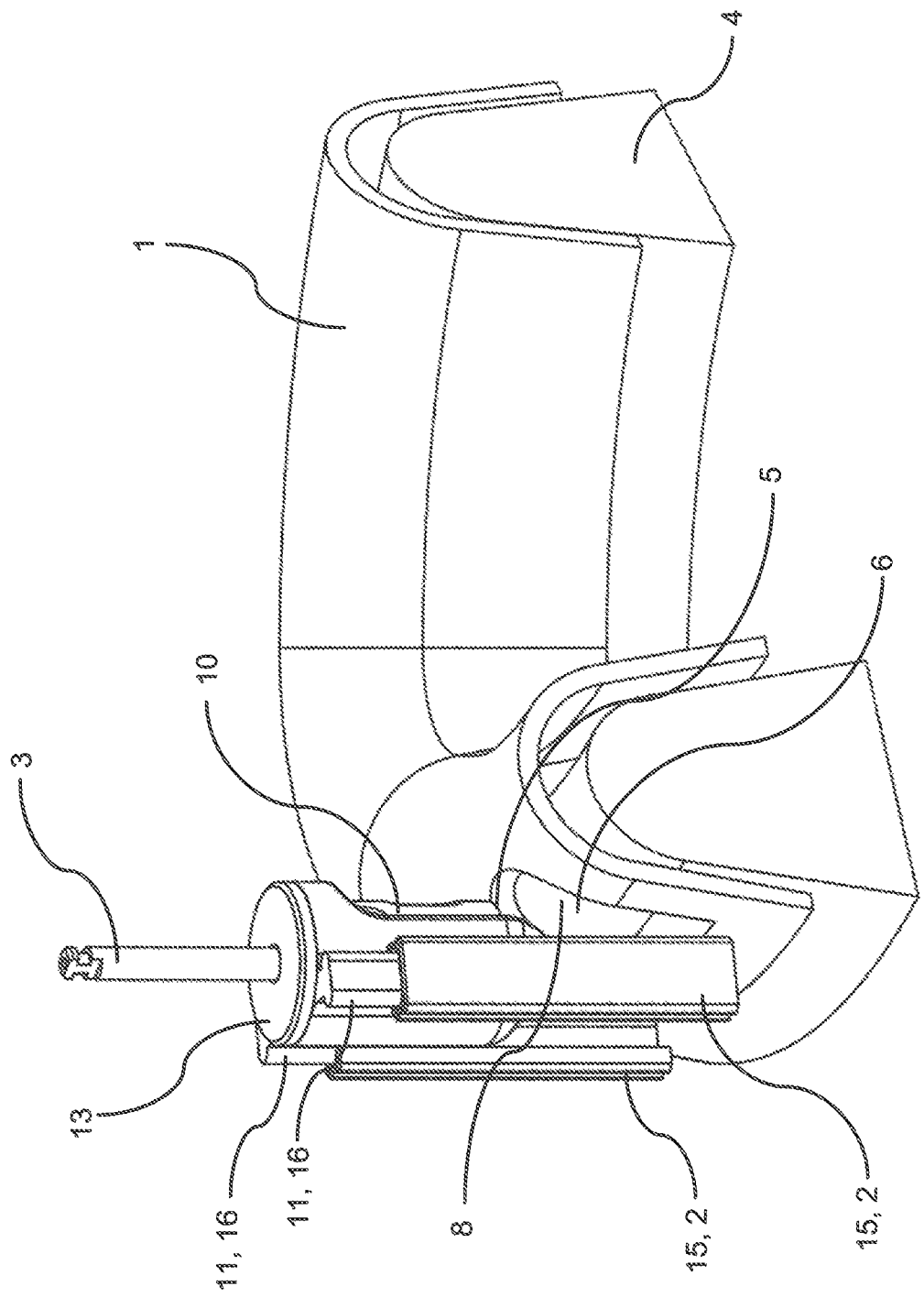
FIG. 5 shows a schematic, perspectival view of another exemplary embodiment of a device according to the present disclosure.
Figure 6:
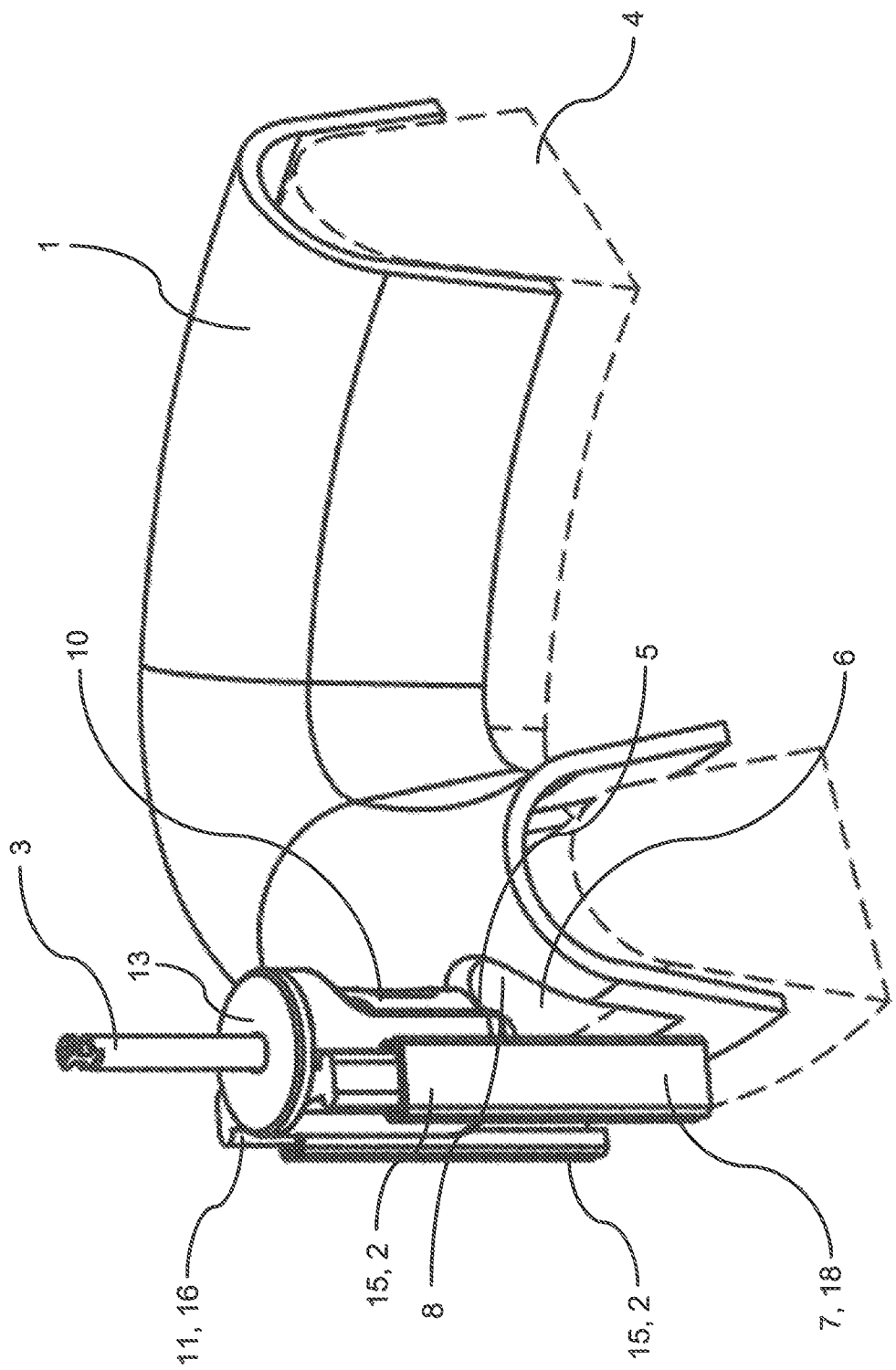
FIG. 6 shows another schematic, perspectival view of the exemplary embodiment according to FIG. 5.

FIGS. 5 and 6 show another exemplary embodiment of a device according to the present disclosure. In this case, the guiding means 2 of the template 1 is realized by two rails 15 or female parts. The hollow bur 3 is rotatably coupled to a protective device 13, wherein guiding elements 11 are formed on the protective device 13 as rails 16 or male parts, which correspond to the rails 15 of the template 1. The hollow bur 3 is thus guided via the rails 15, 16. The protective device 13 otherwise corresponds to the protective device 13 shown in FIGS. 3 and 4.

Figure 7:
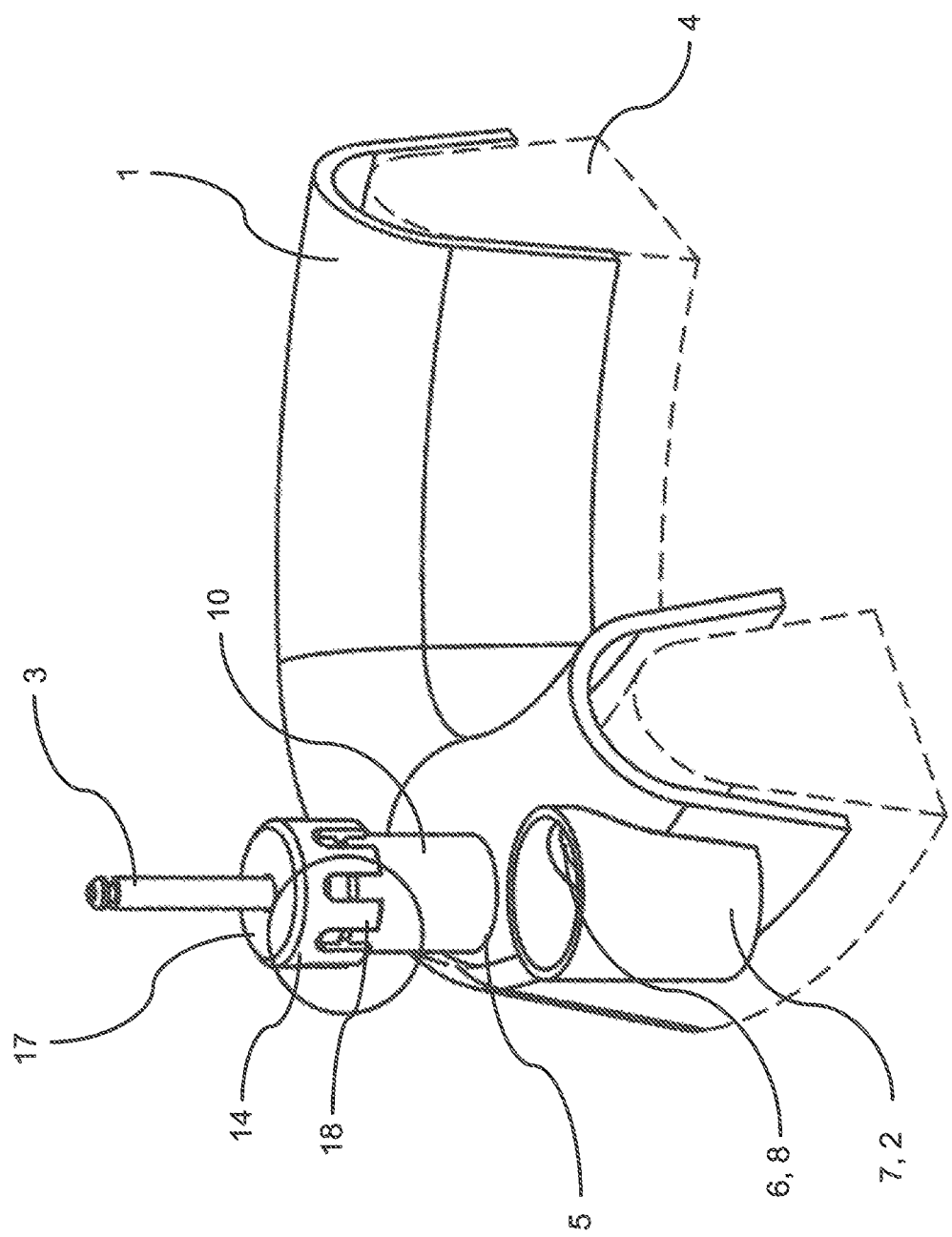
FIG. 7 shows a schematic, perspectival view of another exemplary embodiment of a device according to the present disclosure.
Figure 8:
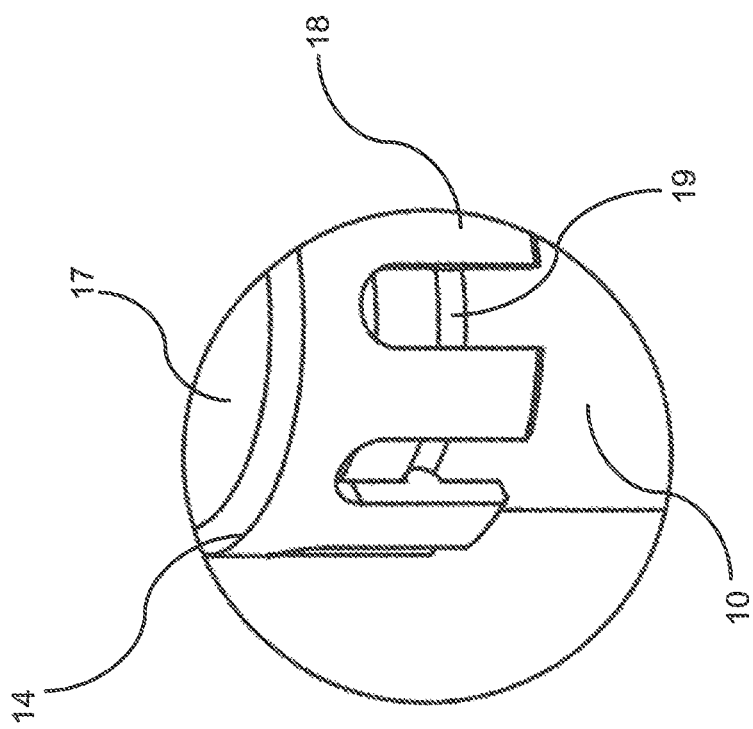
FIG. 8 shows an enlarged partial section of FIG. 7.

The exemplary embodiment of the device according to the present disclosure shown in FIGS. 7 and 8 corresponds to the device shown in FIGS. 3 and 4, such that reference is made to the figure description of FIGS. 3 and 4 in order to avoid repetition. The hollow bur 3 is rotatably connected to a spacer element 14. The outer diameter of the spacer element 14 approximately corresponds to the inner diameter of the guiding sheath 7. The spacer element 14 prevents the head 10 from coming into contact with the guiding sheath 7. The spacer element 14 has a bottom element 17, on which several fixing elements 18 are formed. The fixing elements 18 engage in a groove 19 of the head 10. The spacer element 14 thus surrounds the head 10 in sections and is rotatably coupled to it. The guiding sheath 7 ideally protects the surrounding tissue against injuries caused by the hollow bur 3. In this case, the fixing elements 18 may, where appropriate, protrude further in the direction of the distal edge 5 of the hollow bur 3, wherein at least one fixing element 18—preferably, 3 fixing elements 18—are formed. It is essential that the fixing elements 18 extend far enough over the head 10 that the hollow bur 3 is securely guided within the guiding sheath 7.

Figure 9:
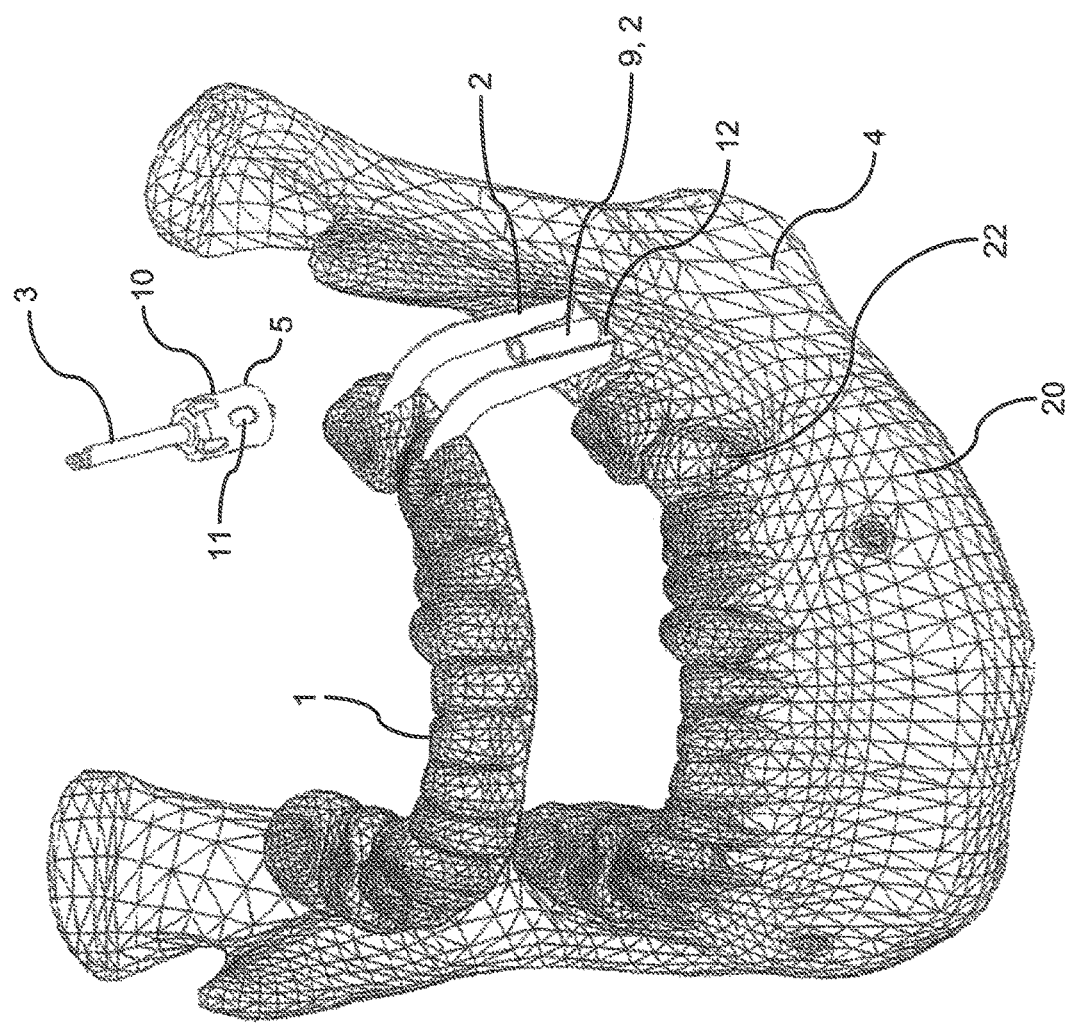
FIG. 9 shows a schematic, perspectival view of another exemplary embodiment of a device according to the present disclosure.
Figure 10:
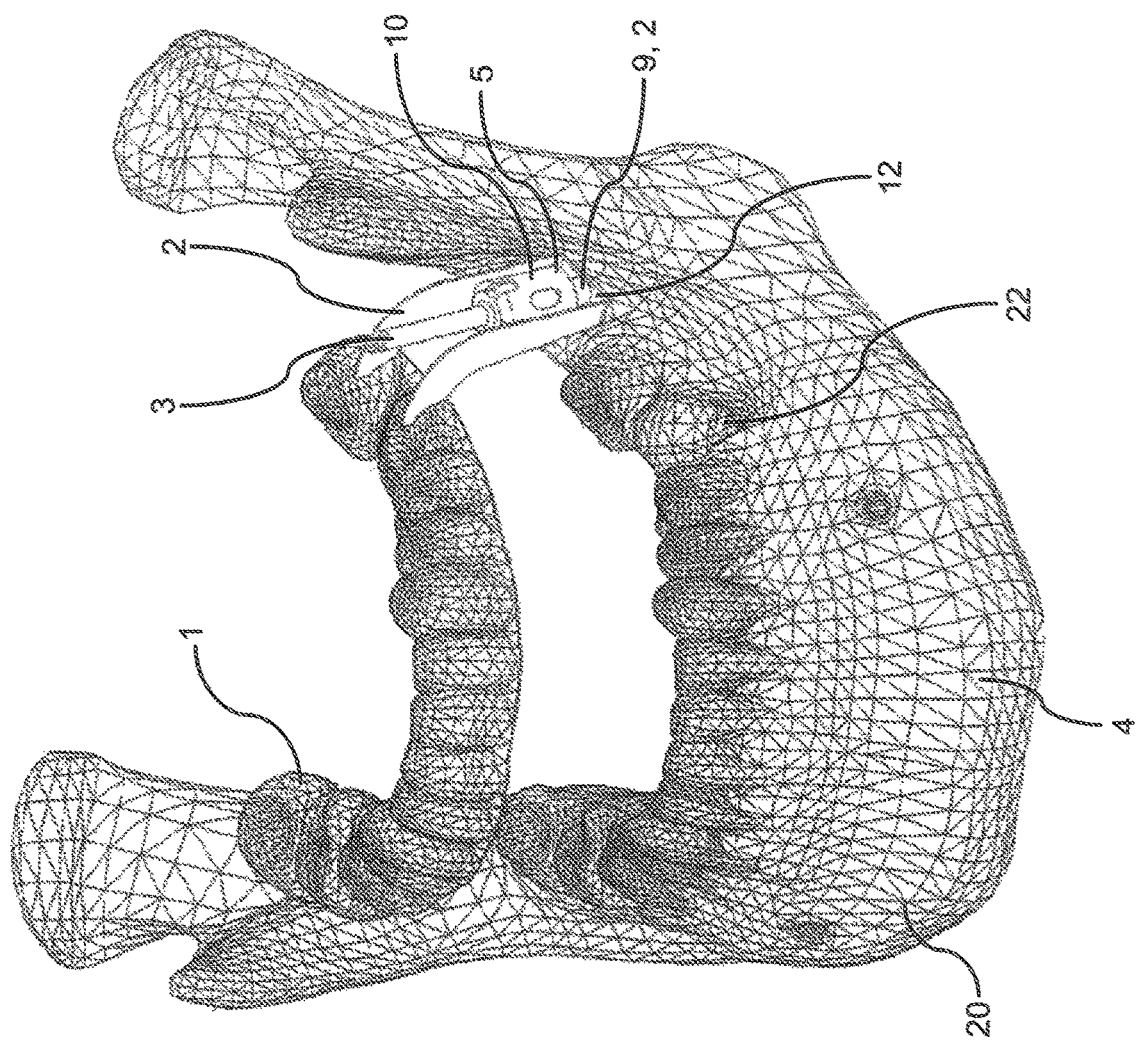
FIG. 10 shows another schematic, perspectival view of the exemplary embodiment according to FIG. 9.
Figure 11:
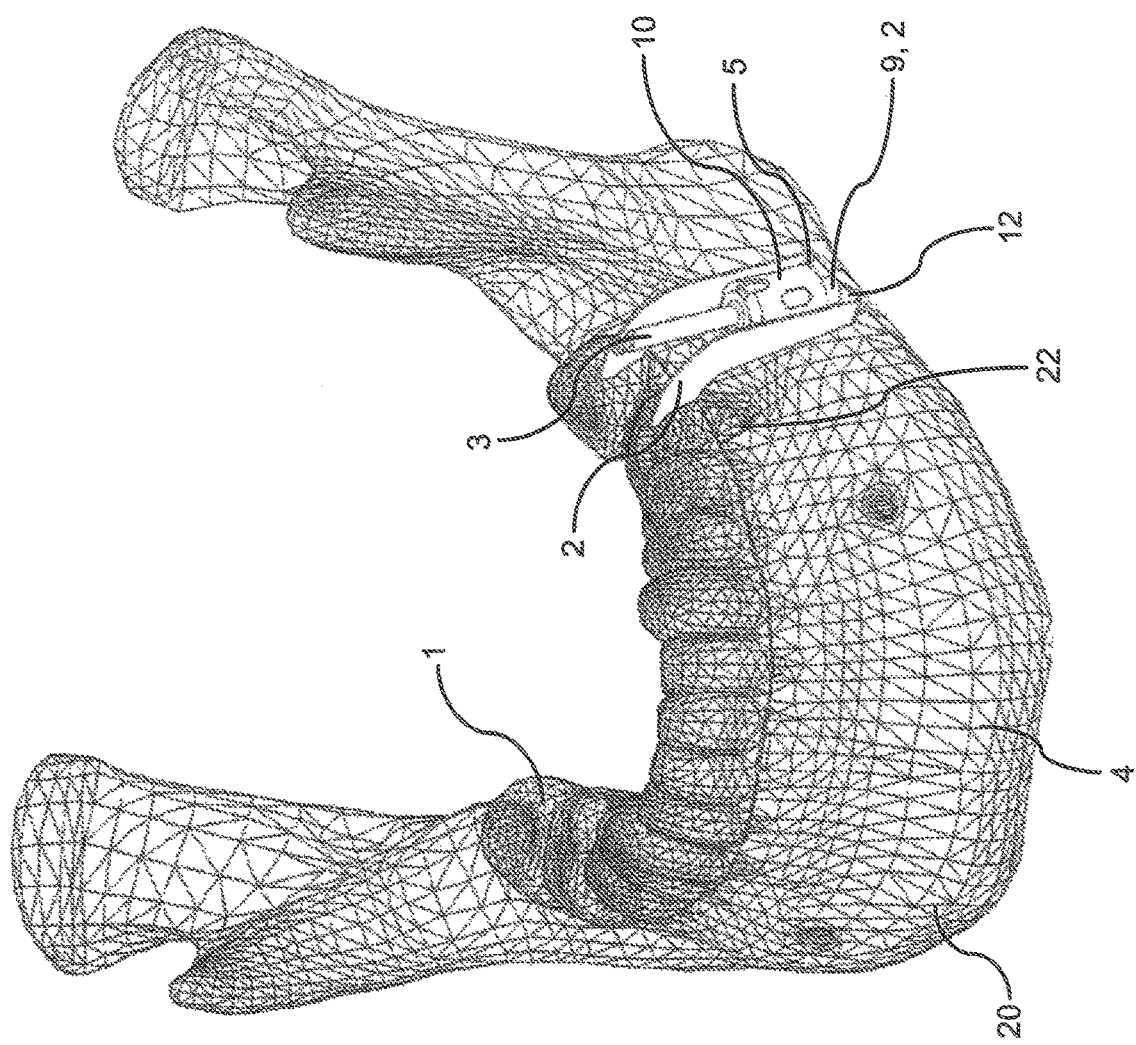
FIG. 11 shows another schematic, perspectival view of the exemplary embodiment according to FIG. 9.

In the exemplary embodiment shown in FIGS. 9 through 11, the guiding means 2 has a receptacle 9 for the guiding element 11 of the head 10 and is connected to the template 1. The template 1 can be arranged in a form-fit or force-fit manner on the teeth of the lower jaw 20 shown. As a result of the design of the guiding means 2, the hollow bur 3 is guided along the bone 4 so that a bone segment can be extracted. In this respect, it is conceivable that the guiding means 2 be designed detachably or non-detachably with the template 1. Furthermore, reference is made to the previous figure description, which analogously applies to the exemplary embodiment of FIGS. 9 through 11.

Figure 12:
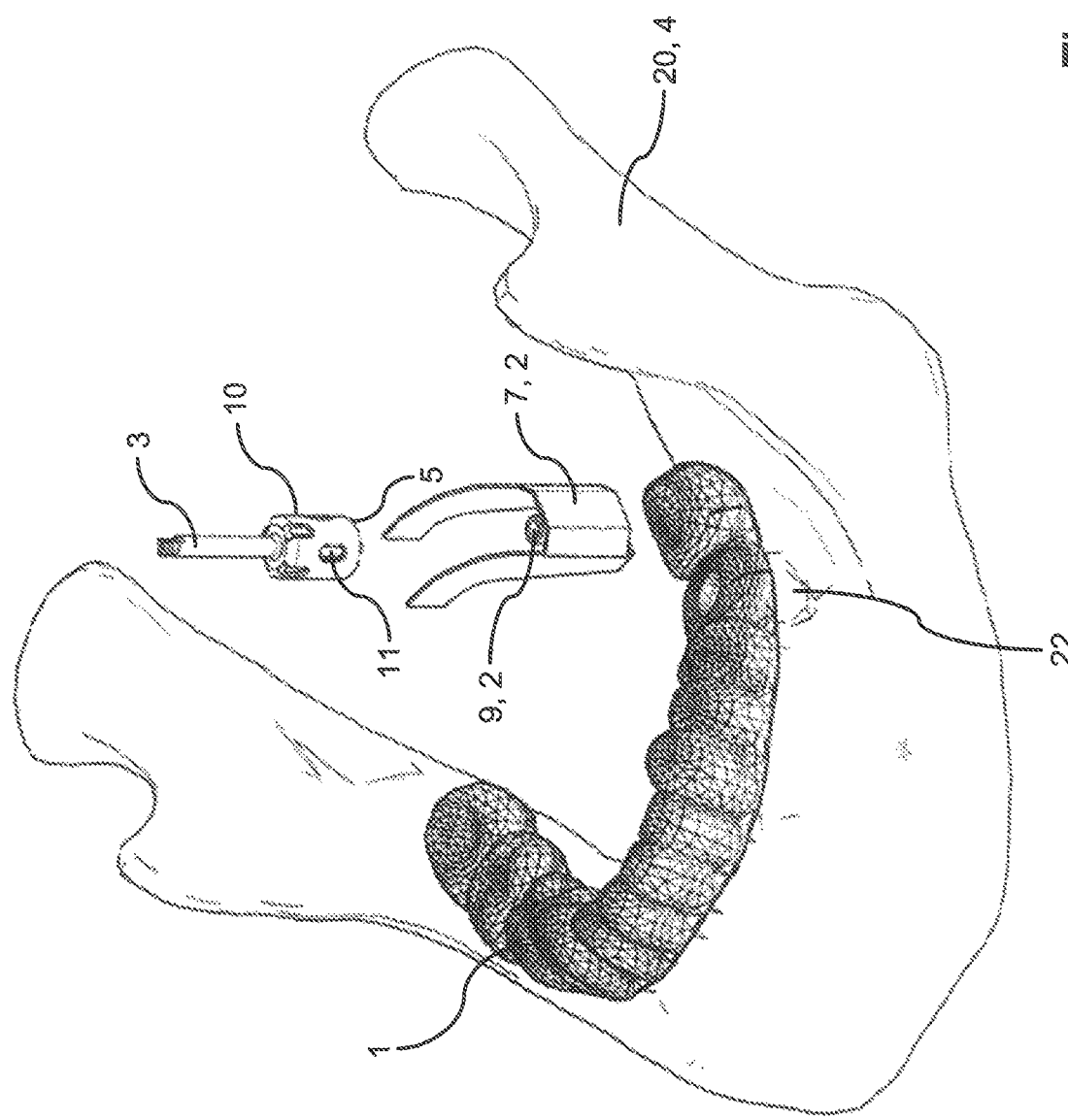
FIG. 12 shows a schematic, perspectival exploded view of another exemplary embodiment of a device according to the present disclosure.
Figure 13:
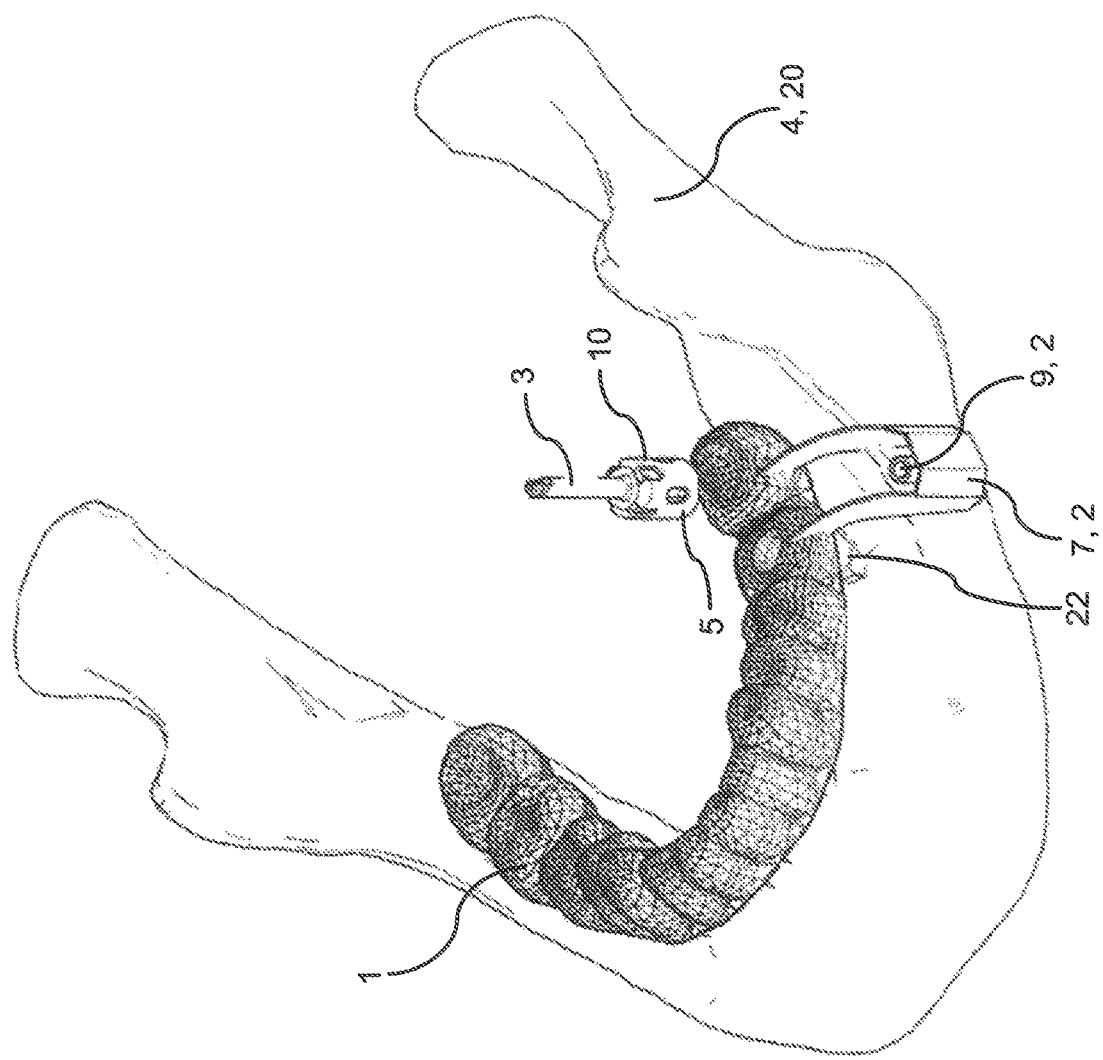
FIG. 13 shows another schematic, perspectival view of the exemplary embodiment according to FIG. 12.
Figure 14:
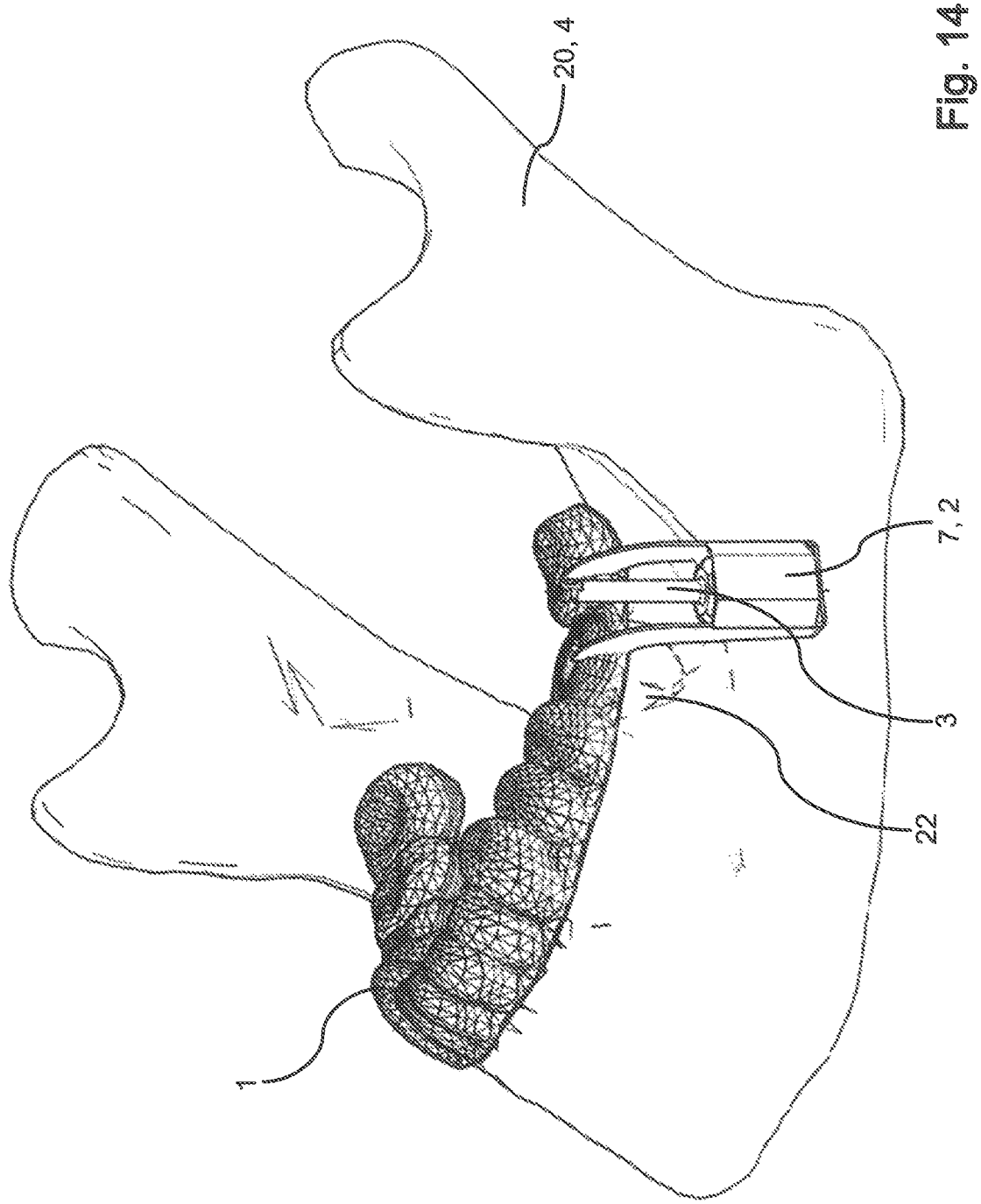
FIG. 14 shows another schematic, perspectival view of the exemplary embodiment according to FIG. 12.

The exemplary embodiment shown in FIGS. 12 through 14 corresponds to the exemplary embodiment shown in FIGS. 9 through 11, wherein the guiding means 2 is additionally designed as guiding sheath 7 along with the receptacle 9. In this case, the guiding sheath 7 has an angular geometry and serves, in particular, to protect the surrounding tissue. It is furthermore pointed out that the guiding sheath 7 can be designed to be closed at its bottom 21. It is, in particular, conceivable that the guiding means 2 be designed detachably or non-detachably with the template 1.

Figure 15:
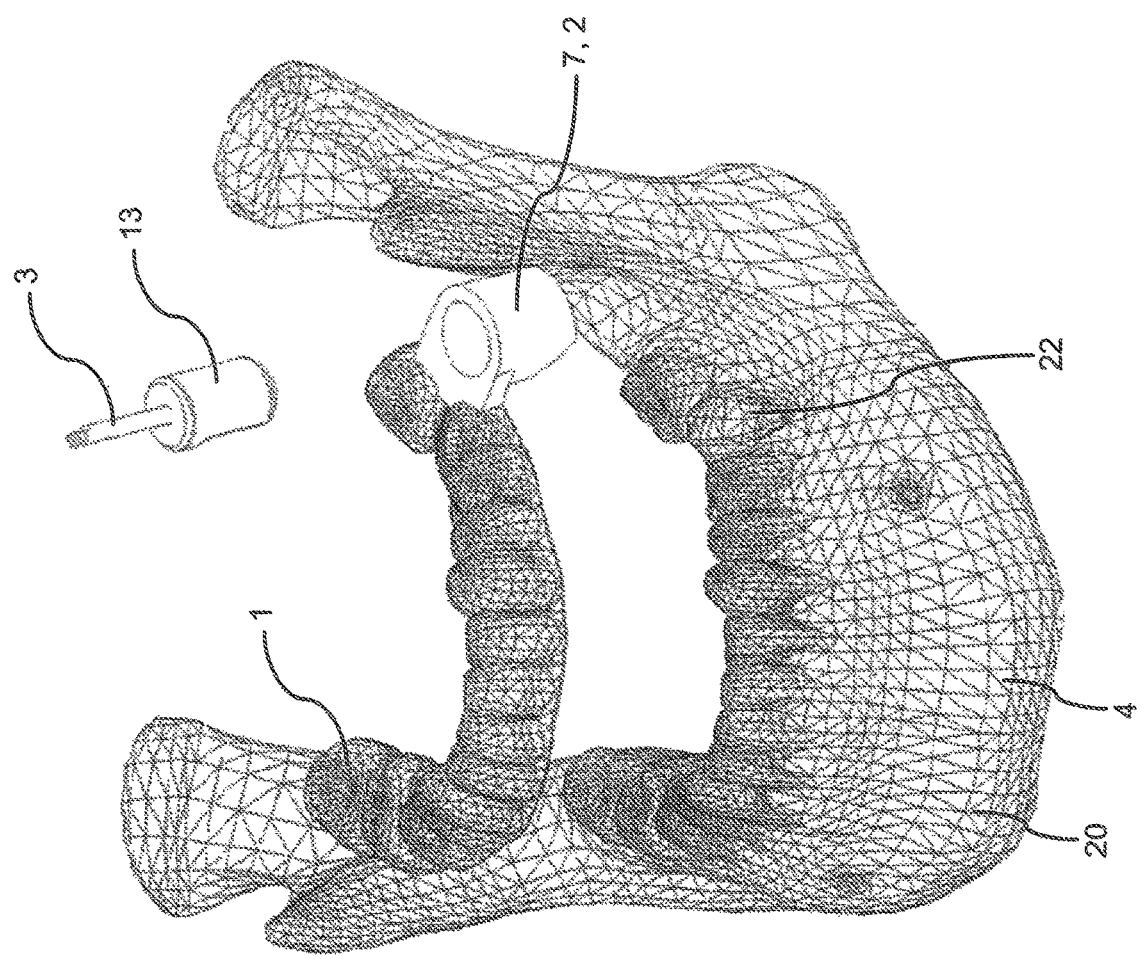
FIG. 15 shows a schematic, perspectival view of another exemplary embodiment of a device according to the present disclosure.
Figure 16:
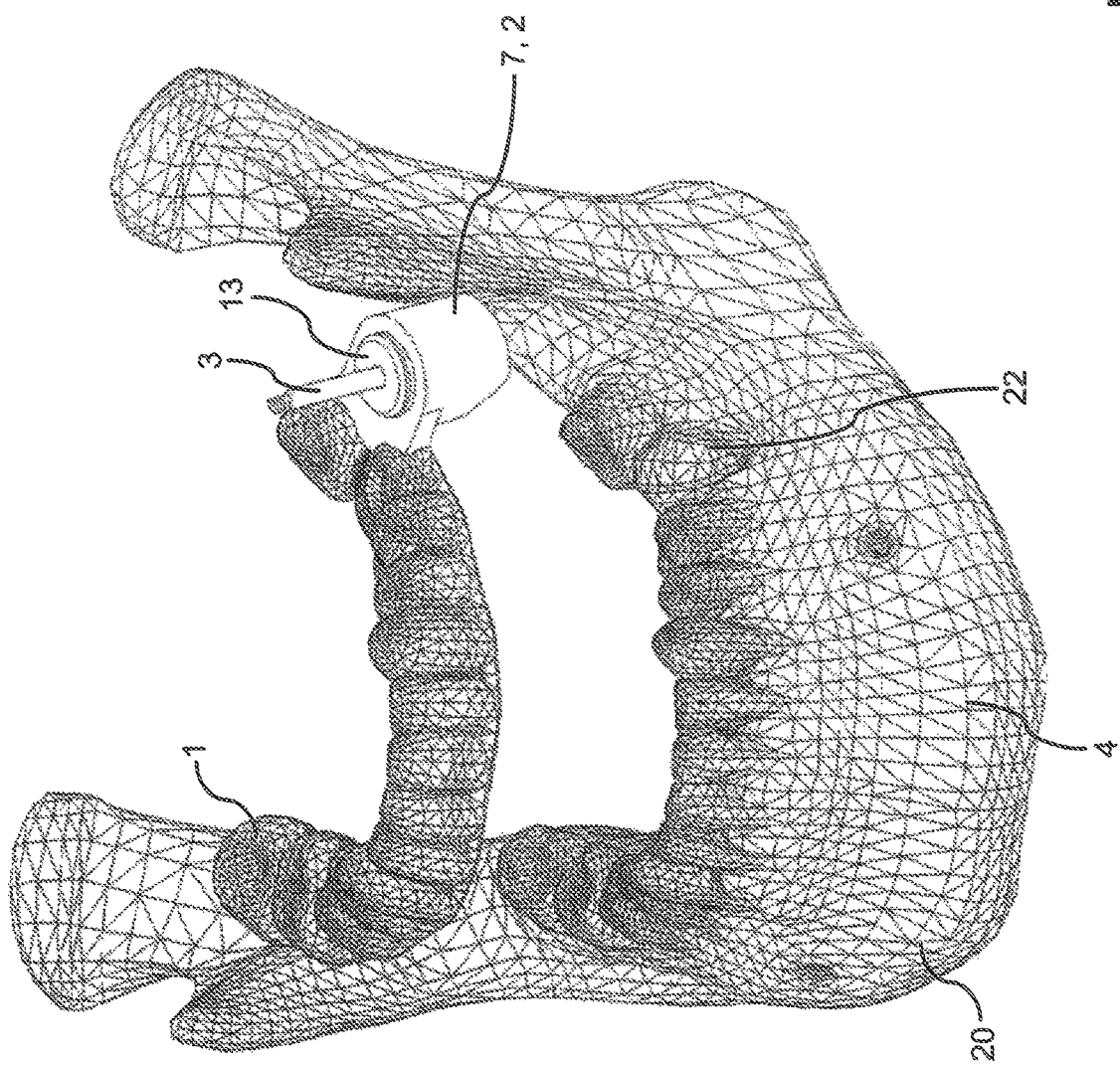
FIG. 16 shows another schematic, perspectival view of the exemplary embodiment according to FIG. 15.
Figure 17:
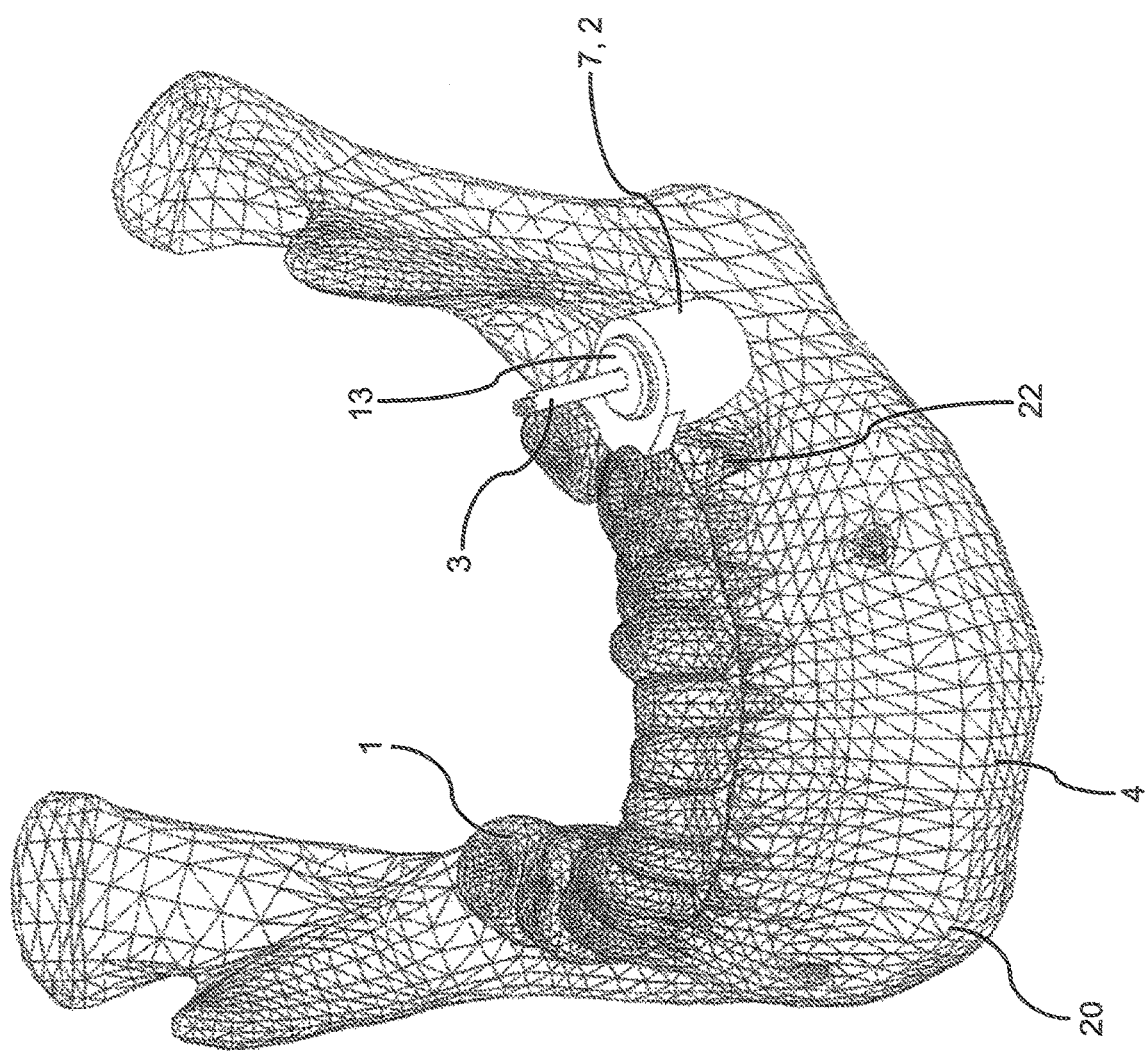
FIG. 17 shows another schematic, perspectival view of the exemplary embodiment according to FIG. 15.
Figure 18:
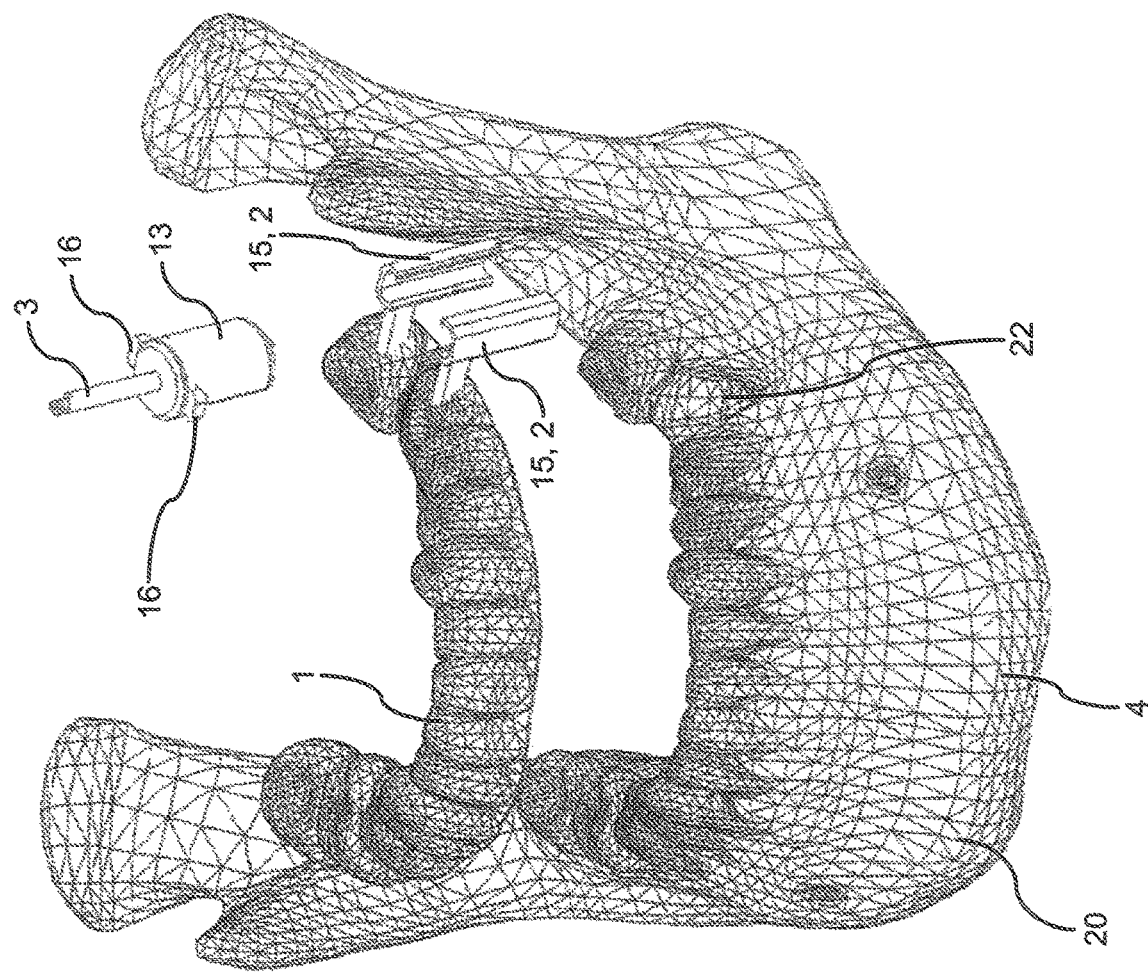
FIG. 18 shows a schematic, perspectival view of another exemplary embodiment of a device according to the present disclosure.
Figure 19:
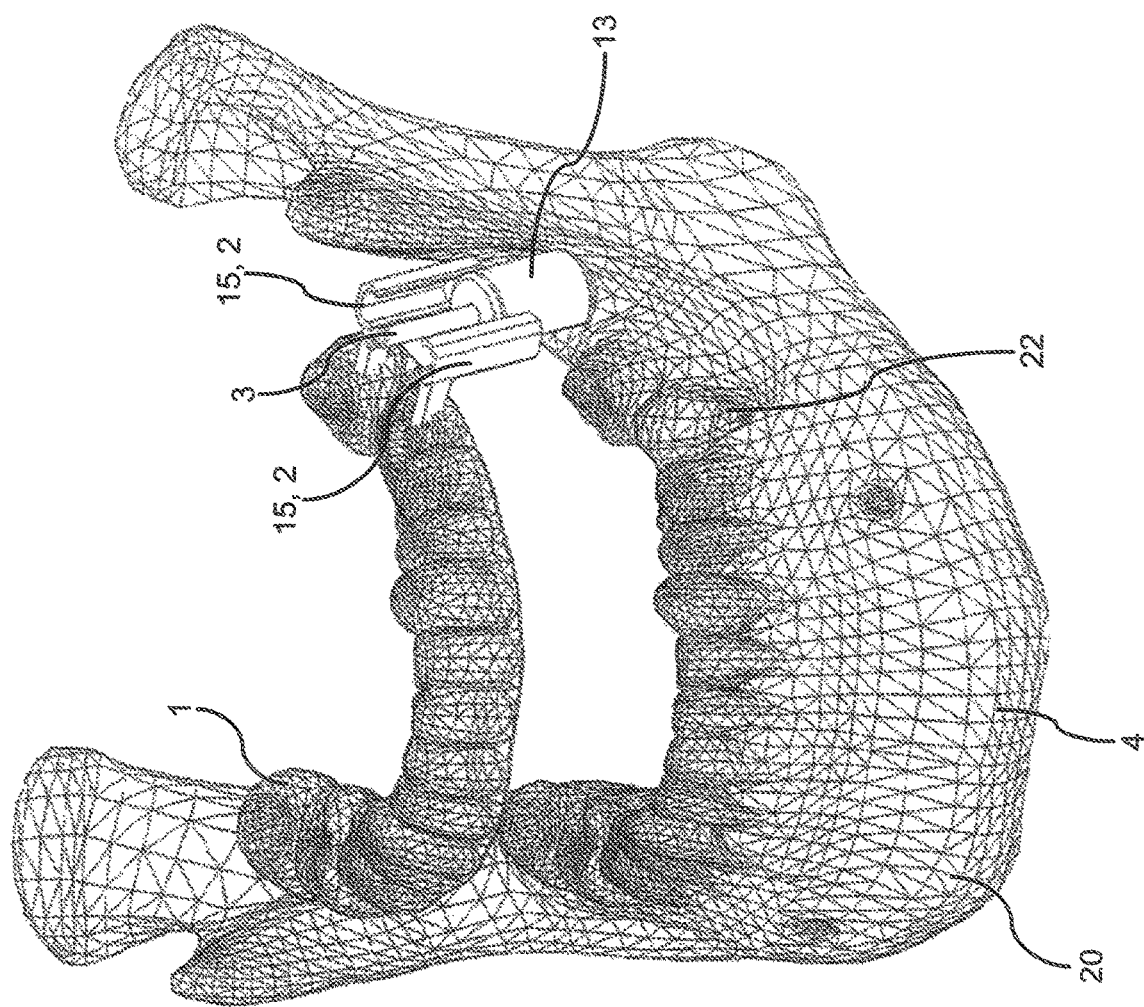
FIG. 19 shows another schematic, perspectival view of the exemplary embodiment according to FIG. 18.

The exemplary embodiment according to FIGS. 15 through 17 substantially corresponds to the exemplary embodiment according to FIGS. 3 and 4. The exemplary embodiment according to FIGS. 18 through 20 furthermore substantially corresponds to the device shown in FIGS. 5 and 6. In order to avoid repetition, reference is made at this point to the figure description above, wherein the guiding means 2 can respectively be designed detachably or non-detachably with the template 1.

The templates 1 shown in FIGS. 1 through 20 can be produced by the method according to the present disclosure. In doing so, a three-dimensional imaging process is carried out first in order to obtain three-dimensional data of the jaw bone 4 or of the extraction point 6 and, where applicable, of the bone deficit 22. Using the three-dimensional data, a three-dimensional computer model of the jaw bone 4 is created. Based upon the computer model, the extraction point 6 can be determined, viz., taking into account the patient-specific anatomy. Based upon the computer model, it is thus determined how the patient-specific template 1 must be designed for the procedure—in particular, where or at which angle the guiding means 2 must be formed on the template 1 and how they must be dimensioned. In the process, the design of the or several guiding means 2 and/or can, where appropriate, also. Based upon the three-dimensional computer model, a patient-specific device can thus be produced. This can, for example, be done in the rapid prototyping process.

Finally, it is expressly pointed out that the above-described exemplary embodiments of the device according to the present disclosure and the method according to the present disclosure serve only to explain the claimed teaching, but do not restrict it to the exemplary embodiments.

LIST OF REFERENCE SYMBOLS

1 Template
2 Guiding means
3 Hollow bur
4 Jaw bone
5 Distal edge
6 Extraction point
7 Guiding sheath
8 Opening
9 Receptacle
10 Head
11 Guiding element
12 Depth stopper
13 Protective device
14 Spacer element
15 Rails (guiding means)
16 Rails (protective device)
17 Bottom element
18 Fixing elements
19 Groove
20 Lower jaw
21 Bottom
22 Bone deficit

The invention claimed is:

1. An apparatus for bone extraction, comprising:
a dental-surgical hollow bur configured to extract bone in the shape of a circular segment; and
a device that guides the dental-surgical hollow bur during a bone extraction, the device having a template that is fixable in a region of an extraction point and having at least one guiding sheath arranged on the template, wherein the guiding sheath is, at least in part, spaced laterally outward from an opening in the template through which the hollow bur can be brought into contact with the bone to be extracted, wherein the guiding sheath is sized and configured to receive the hollow bur and guide the hollow bur such that only a portion of a distal edge of the hollow bur can be brought through the opening in the template into contact with the bone, and wherein, during a bone extraction, the hollow bur is guided laterally along the bone so that a piece of the bone in the shape of a circular segment is extracted.

2. The apparatus according to claim 1, wherein the template is fixable in the upper jaw or in the lower jaw in a form-fit and/or force-fit manner.

3. The apparatus according to claim 1, wherein the guiding sheath surrounds the hollow bur such that tissue surrounding the extraction point does not come into contact with the hollow bur.

4. The apparatus according to claim 1, wherein the template further comprises a receptacle for receiving a corresponding guiding element of the hollow bur.

5. The apparatus according to claim 1, wherein the template further comprises a depth stopper for the hollow bur so that the distal edge of the hollow bur can be brought into contact with the bone only over a defined length.

6. The apparatus according to claim 1, wherein the guiding sheath is detachably connected to the template.

7. The apparatus according to claim 1, wherein the guiding sheath is a single piece with the template or is an integral part of the template.

8. The apparatus according to claim 1, wherein the guiding sheath has a coupling element that detachably fixes the guiding sheath on the template.

9. The apparatus according to claim 1, wherein the template has a coupling element that detachably fixes the guiding sheath to the template.

10. The apparatus according to claim 1, wherein an inner diameter of the guiding sheath is dimensioned such that the hollow bur does not come into contact with the guiding sheath.

11. An apparatus for bone extraction, comprising:
a dental-surgical hollow bur configured to extract bone in the shape of a circular segment; and
a device that guides the dental-surgical hollow bur during a bone extraction, the device having a template that is fixable in a region of an extraction point and having at least one guiding receptacle arranged on the template, wherein the receptacle is positioned with respect to an opening in the template through which the hollow bur can be brought into contact with the bone to be extracted, wherein the receptacle is sized and configured to receive a corresponding guiding pin of the hollow bur and guide the hollow bur such that only a portion of a distal edge of the hollow bur can be brought through the opening in the template into contact with the bone, and wherein, during a bone extraction, the hollow bur is guided laterally along the bone so that a piece of the bone in the shape of a circular segment is extracted.

12. The apparatus according to claim 11, wherein the template is fixable in the upper jaw or in the lower jaw in a form-fit and/or force-fit manner.

13. The apparatus according to claim 11, wherein the guiding pin extends axially from within a head of the hollow bur.

14. The apparatus according to claim 11, wherein receptacle is a circular cylinder or tube.

15. The apparatus according to claim 11, further comprising a guiding sheath that is, at least in part, spaced laterally outward from the opening in the template, wherein the guiding sheath is sized and configured to receive the hollow bur and further guide the hollow bur such that only a portion of the distal edge of the hollow bur can be brought into contact with the bone.

16. The apparatus according to claim 15, wherein the guiding sheath surrounds the hollow bur such that tissue surrounding the extraction point does not come into contact with the hollow bur.

17. The apparatus according to claim 15, wherein the guiding sheath is a single piece with the template or is an integral part of the template.

18. The apparatus according to claim 15, wherein an inner diameter of the guiding sheath is dimensioned such that the hollow bur does not come into contact with the guiding sheath.

19. The apparatus according to claim 15, further comprising a coupling element that detachably fixes the guiding sheath on the template.

20. The apparatus according to claim 11, wherein the template further comprises a depth stopper for the hollow bur so that the distal edge of the hollow bur can be brought into contact with the bone only over a defined length.

\* \* \* \* \*